United States Patent
Kim (10) Patent No.: US 7,564,945 B2
(45) Date of Patent: Jul. 21, 2009

(54) SYSTEM INCLUDING COMPUTED TOMOGRAPHY DEVICE FOR IMAGE GUIDED TREATMENT

(75) Inventor: Siyong Kim, Jacksonville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/814,687

(22) PCT Filed: Feb. 13, 2006

(86) PCT No.: PCT/US2006/004998
§ 371 (c)(1),
(2), (4) Date: Jul. 25, 2007

(87) PCT Pub. No.: WO2006/086765
PCT Pub. Date: Aug. 17, 2006

(65) Prior Publication Data
US 2008/0205588 A1 Aug. 28, 2008

Related U.S. Application Data

(60) Provisional application No. 60/652,085, filed on Feb. 11, 2005.

(51) Int. Cl.
*A61N 5/10* (2006.01)
*A61B 6/03* (2006.01)
*H05G 1/02* (2006.01)

(52) U.S. Cl. .......................... 378/65; 378/17; 378/196; 378/197

(58) Field of Classification Search .............. 378/9, 378/15, 17, 20, 65, 68, 69, 195, 196, 197, 378/198; 600/425, 427
See application file for complete search history.

(56) References Cited

U.S. PATENT DOCUMENTS

| | | | | |
|---|---|---|---|---|
| 5,537,452 A | * | 7/1996 | Shepherd et al. | 378/65 |
| 5,572,567 A | * | 11/1996 | Khutoryansky et al. | 378/197 |
| 5,751,781 A | * | 5/1998 | Brown et al. | 378/65 |
| 6,400,791 B1 | * | 6/2002 | Schwarz | 378/17 |
| 6,490,476 B1 | * | 12/2002 | Townsend et al. | 600/427 |
| 6,580,777 B1 | * | 6/2003 | Ueki et al. | 378/17 |
| 6,614,871 B1 | * | 9/2003 | Kobiki et al. | 378/20 |
| 6,754,519 B1 | * | 6/2004 | Hefetz et al. | 600/407 |
| 6,754,520 B2 | * | 6/2004 | DeSilets et al. | 600/415 |
| 6,831,961 B1 | * | 12/2004 | Tybinkowski et al. | 378/4 |

(Continued)

Primary Examiner—Allen C. Ho
(74) Attorney, Agent, or Firm—Novak Druce + Quigg LLP; Gregory A. Nelson; Gregory M. Lefkowitz (57) ABSTRACT

A computed tomography (CT) system (300) includes a table (304) for holding a patient (302), a first gantry (311) for holding a radiation source (310) which emits penetrating radiation, and a second gantry (313) spaced apart from the first gantry holding a penetrating radiation detector (312) for receiving the penetrating radiation after passing through the patient. The penetrating radiation from the radiation source is angled at a non-perpendicular angle with respect to a longitudinal axis (322) of the table. A third gantry (320) is spaced apart from the first and second gantry including at least one radiation therapy source (321) or other (non-CT) imaging system, wherein the third gantry is located between the first gantry and the second gantry. The CT system thus permits computed tomography to occur simultaneously or substantially simultaneously with other procedures, such as various other radiation therapy systems, imaging modality or surgical procedures.

16 Claims, 5 Drawing Sheets

U.S. PATENT DOCUMENTS

| | | | |
|---|---|---|---|
| 6,865,254 B2 * | 3/2005 | Nafstadius | 378/65 |
| 6,961,606 B2 * | 11/2005 | DeSilets et al. | 600/415 |
| 7,162,004 B2 * | 1/2007 | Inoue et al. | 378/4 |
| 7,254,438 B2 * | 8/2007 | DeSilets et al. | 600/427 |
| 2004/0005027 A1 | 1/2004 | Nafstadius | |

* cited by examiner

FIG. 5

SYSTEM INCLUDING COMPUTED TOMOGRAPHY DEVICE FOR IMAGE GUIDED TREATMENT

CROSS-REFERENCE TO RELATED APPLICATIONS

This application is the national stage entry of International Application No. PCT/US2006/004998, filed Feb. 13, 2006, which claims priority to U.S. Provisional Patent Application No. 60/652,058, filed Feb. 11, 2005.

FIELD OF THE INVENTION

The present invention relates to computerized tomography. More specifically, the present invention relates to computerized tomography devices that permit computerized tomography to be performed substantially simultaneously with other radiation and/or surgical procedures.

BACKGROUND OF THE INVENTION

In recent years, much interest has been evidenced in a field now widely known as computed tomography. In a typical procedure utilizing computed tomography (or CT), an X-ray source and detector are physically coupled together on opposite sides of the portion of a sample which is to be examined. The sample may be, for example, a patient or phantom or other objects. X-rays are made to transit through the sample to be examined, while the detector measures the X-rays which make it through the sample without being absorbed or deflected. Periodically, the paired source and detector are rotated to differing angular orientations about the sample, and the data collection process repeated.

A very high number of measurements of attenuation values may be obtained by procedures of this type. The relatively massive amounts of data thus accumulated are processed by a computer, which typically does a mathematical data reduction to obtain attenuation values for a very high number of transmission values (typically in the hundreds of thousands) within the section of the sample being scanned. This data may then be combined to enable reconstruction of a matrix (visual or otherwise) that constitutes an accurate depiction of the density function of the sample section examined.

By considering one or more of such sections, skilled medical diagnosticians may diagnose various body elements such as tumors, blood clots, cysts, hemorrhages and various abnormalities, which, heretofore, were detectable, if at all, only by much more cumbersome and, in many instances, more hazardous techniques to the patient.

While systems of the aforementioned type have represented powerful diagnostic tools, and were deemed great advances in the radiography art, first generation systems suffered from many shortcomings. Acquisition of the raw data frequently entailed an undesirably long period, which, among other things, subjected a patient to both inconvenience and stress. The patient's inability to remain rigid for such a lengthy period, also led to blurring of the image sought to be obtained.

Radiation therapy is another aspect having a great deal of interest. Conventional radiation therapy techniques typically involve directing a radiation beam at a tumor in a patient to deliver a predetermined dose of therapeutic radiation to the tumor according to an established treatment plan. This is typically accomplished using a radiation therapy device.

Tumors have three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

In many radiation therapy devices, the treatment beam is projected through a pre-patient collimating device (a "collimator"), which defines the treatment beam profile or the treatment volume at the treatment zone. A number of different collimator techniques have been developed to attempt to conform the dose rate and the treatment volume to the shape of the tumor while taking nearby healthy tissue and organs into account. A first technique is to use a collimator with solid jaw blocks positioned along a path of the treatment beam to create a field shape based on the shape of the tumor to be treated. Typically, two sets of blocks are provided, including two blocks making up a Y-jaw generally disposed parallel to a Y-axis (with the Z-axis being parallel to the beam path), and two blocks making up an X-jaw generally disposed parallel to an X-axis. The X-jaw is conventionally placed between the Y-jaws and the patient.

These solid jaw blocks, however, do not provide sufficient variability in the field shape. In particular, where the tumor has a shape which requires a field edge relatively parallel to the edge of the jaw blocks, the edge of the jaw block becomes more predominant in forming the field edge. As a result, undulation of the field increases as well as the effective penumbra. This can be particularly difficult where the treatment beam is an X-ray beam. It is also difficult to adjust the field shape where the treatment beam is an electron beam due to electron attenuation and scattering.

In a typical radiation therapy device, a frame housing the linear accelerator (X-ray tube) and collimators having a large opening into which the patient is inserted (referred to herein as a gantry) is swiveled around a horizontal axis of rotation in the course of a therapeutic treatment of the patient. The linear accelerator generates a high-energy radiation beam (referred to herein as a "photon beam" or "photons") for use in the therapeutic treatment.

Historically, linear accelerators used in radiation therapy applications have been equipped to provide only a single energy photon beam. In the recent past, however, some linear accelerators have been equipped to provide two different energy beams. The limited number of energies available is a continuing problem for physicians and physicists, since it is not always possible for them to give the most efficacious treatments. Currently, certain manufacturers are attempting to provide linear accelerators with the capability of generating three different photon energies. Such machines, however, will still preclude much other intermediate energy that may be useful.

A therapeutic x-ray beam produced by a linear accelerator is characterized by the amount of energy that will be deposited at a treatment site by that particular x-ray beam. This characterization relates to the depth (usually measured from the surface of the skin) at which the beam's maximum energy is deposited (often referred to in the art as "dmax").

Nevertheless, these radiation technologies do not permit the system to be able to perform simultaneous treatment of an area using different types of radiation treatments. Additionally, none of these systems and methods permit computerized tomography to occur during treatment, thereby leading to more accurate treatment of the patient.

Accordingly, it would be beneficial to provide a system that permitted multiple types of radiation therapy to be performed simultaneously. It would also be beneficial to provide a system that was capable of performing radiation therapy with computerized tomography to permit more accurate treatment.

SUMMARY OF THE INVENTION

A computed tomography (CT) system includes a table for holding a patient, a first gantry for holding a radiation source which emits penetrating radiation, and a second gantry spaced apart from the first gantry holding a penetrating radiation detector which receives the penetrating radiation after passing through and being attenuated by the patient. The penetrating radiation from the radiation source is angled at a non-perpendicular angle with respect to a longitudinal axis of the table. When used for radiation therapy, systems according to the invention thus provide independent CT because the source trajectory can be different for the therapy beam and the imaging beam.

The system can further comprise a third gantry spaced apart from the first and second gantry including at least one radiation therapy source or other imaging system, wherein the third gantry is located between the first and second gantry. The radiation therapy source can be a linear accelerator (X-ray tube) or a radioactive isotope (e.g. cobalt) source. The other (non-CT) imaging system can comprise an emission tomography system, such as a Single Photon-Emission Tomography system or Positron Emission Tomography system.

The third gantry can comprise a plurality of radiation therapy sources. In this embodiment, each of the plurality of radiation therapy sources is preferably provided a multileaf collimator. In one embodiment, the third gantry comprises an outer ring and an inner ring, wherein the inner and outer rings are independently rotatable. The outer ring can includes the plurality of radiation sources and the inner ring comprise a plurality of beam modifier slots. The outer ring can also include a plurality of electrical portal imaging devices (EPIDs).

A method of performing substantially real-time CT image guided treatment on a patient comprises the steps of providing a computed tomography system wherein penetrating radiation from the system is angled at a non-perpendicular angle with respect to a longitudinal axis of a table holding a patient, and performing a treatment or other imaging step on the patient while performing CT imaging using guidance from images generated by the CT system. The treatment step or other imaging step can comprise radiation therapy, emissions tomography, a surgical procedure, or a combination thereof. The treatment step can be radiation therapy delivered by a linear accelerator treatment or a radioactive isotope (e.g. cobalt) source. The other imaging step can comprise emission tomography treatment selected from Single Photon-Emission Tomography or Positron Emission Tomography.

BRIEF DESCRIPTION OF THE DRAWINGS

Other objects, features and advantages of the present invention will become apparent upon reading the following detailed description, while referring to the attached drawings, in which.

DETAILED DESCRIPTION OF THE INVENTION

The present invention is more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of."

In general, a CT scan is an x-ray procedure enhanced by a computer. This results in a three-dimensional view (referred to as a "slice") of a particular part of a patient's body. During a routine x-ray, dense tissues can block other areas. Aided by a computer, a CT scan is able to put together the different "slices" and create a three-dimensional view, clearly showing both bone and soft tissue. Prior art systems performed this system using x-ray imaging that was perpendicular to the patient being examined. Accordingly, during a CT scan, the area being examined cannot be accessed.

The present invention provides a system and method of computerized tomography wherein CT scanning may occur substantially simultaneously as an additional radiation treatment or an additional medical treatment that, heretofore, would have needed to be done separately. The present invention is capable of performing the substantially simultaneous CT scanning using a computerized tomography system referred to herein as a beveled tomography system. As used herein, a beveled computerized tomography system refers to CT comprising system that includes separate gantries for the penetrating radiation (e.g. X-ray) source and for the penetrating radiation detector (e.g. X-ray detector) which angles the penetrating radiation from the radiation source at a non-perpendicular angle with respect to a longitudinal axis of the table holding the patient. As a result, systems according to the invention permit CT to be performed while leaving the area of interest of the patient open, either for radiation therapy and/or for access by medical staff. As such, the present invention sets forth a system and related method that provide one or more advantages compared to known CT systems.

Figure 1:
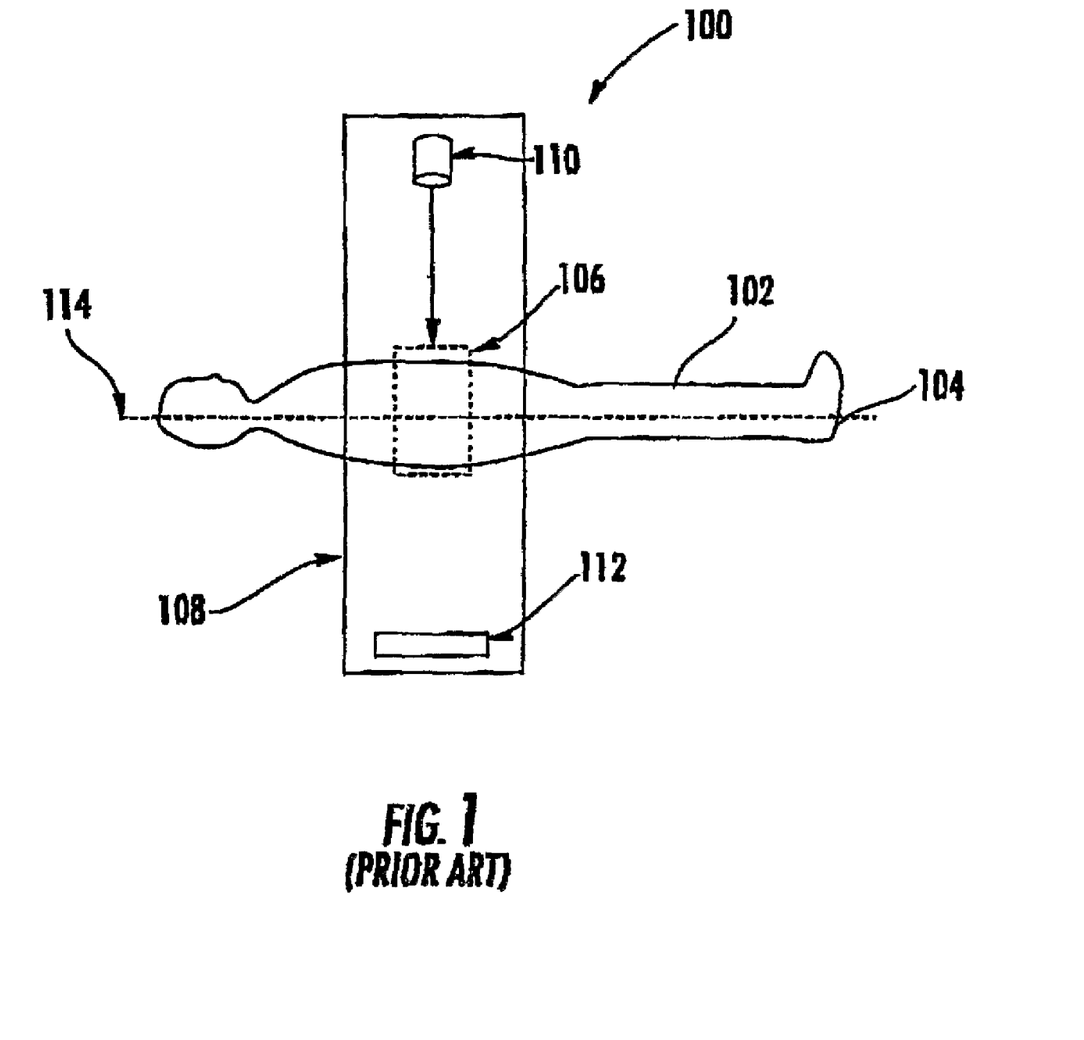
FIG. 1 shows a prior art computerized tomography system.

As may be seen in FIG. 1, a standard CT that is currently available provides a system wherein the center of radiation is incident perpendicularly to the axis of gantry. In this system 100, a patient 102 rests on a table 104. The patient 102 includes a region of interest 106 that is to be subjected to computerized tomography. The CT portion of the system 100 includes a CT gantry 108 having an x-ray source 110 and a detector 112. The x-ray source 110 and detector 112 are located in the CT gantry 108 in a direction perpendicular 114 to the patient 102 on the table 104. As such, there is no room to access to the region of patient 106 that is of interest to medical staffs.

Figure 2:
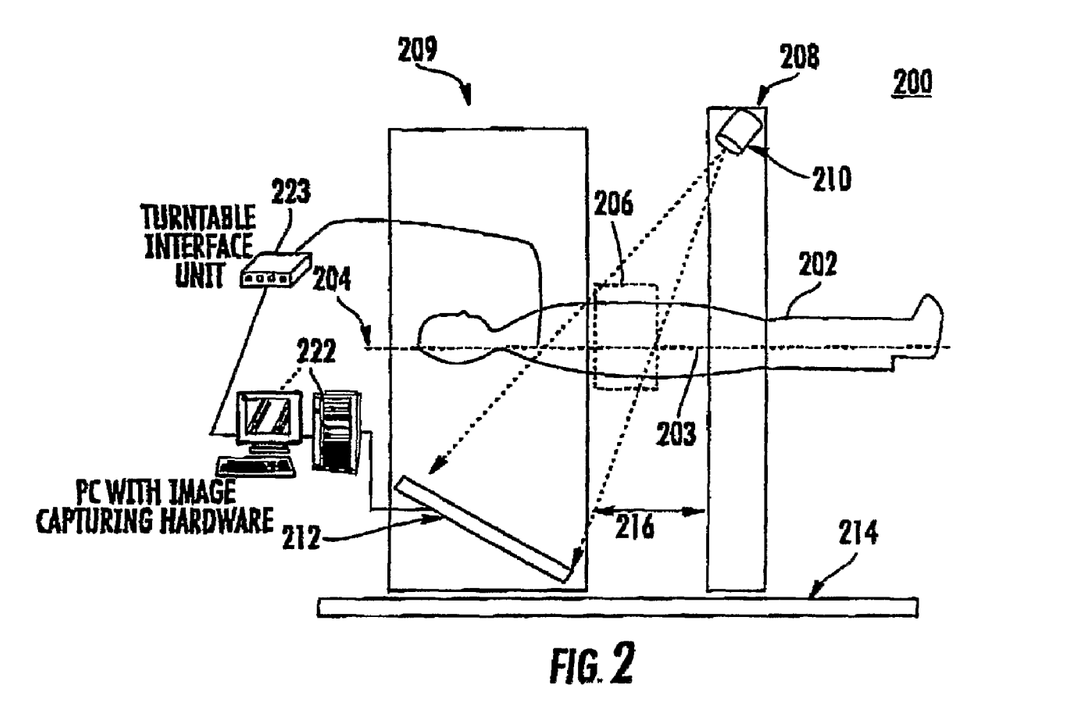
FIG. 2 shows a side view of a beveled computerized tomography system according to one embodiment of the present invention.

Conversely, as shown in FIG. 2, the present invention, in one embodiment, provides a CT system 200 having dual gantries 208 and 209 for imaging patient 202 disposed on a table 203 used to support the patient 202 during the procedure. Table 203 comprises a computer controlled turntable. Gantry 208 controls the position of x-ray source 210 and thus the x-ray beam, while gantry 209 controls the position of detector 212. Accordingly, the rotation plane of detector 212 can be different from that of x-ray source 210. Moreover, emissions from the x-ray source 210 are angled relative to the detector 212. Therefore, imaging x-ray beams are passing through patient 202 with an angle with respect to the longitudinal axis of table 204. Detector 212 includes an image intensifier (not shown).

The analog intensified video signal provided by detector 212 is communicated to PC or other computing structure having image capture hardware 222. The output of PC 222 is communicably connected to turntable interface unit 223 which controls the position of table 203 via computer controlled turntable. PC 222 provides image reconstruction to generate conventional image views by taking the system geometry into account. The resulting design of system 200 permits the medical staff to access to the region of interest 206 of the patient 202. Depending on the design, gantries 208, 209 may be mounted on rails 214 and the width of access area 216 may be adjusted. In these embodiments, angles of x-ray source 210 and detector 212 are designed to be adjustable.

As may be seen from FIG. 2, the x-ray source 210 is angled at an angle that is not perpendicular to the longitudinal axis of table 204. The detection panel 212 is also angled at an angle that is not perpendicular to the longitudinal axis of the table 204. Depending on the selected distance between the gantries 208 and 209, the x-ray source 210 and detection panel 212 may be angled from between about 10 to about 80 degrees with respect to the longitudinal axis of the table 204. In select embodiments, the x-ray source 210 and detection panel 212 may be angled from between about 30 to about 60 degrees with respect to the longitudinal axis of the table 204. In yet other embodiments, the x-ray source 210 and detection panel 212 may be angled from between about 40 to about 50 degrees with respect to the longitudinal axis of the table 204.

Accordingly, in one embodiment of the present invention, a beveled CT system is used in conjunction with a novel radiation therapy (RT) system that enables image guided radiation therapy (IGRT) to be performed. In one embodiment, these systems and methods permit computerized tomographic imaging to occur independently and thus simultaneously during radiation therapy beam delivery. As set forth herein, this may be referred to as "CT-based through-RT IGRT", which refers to a system capable of performing independent CT that is capable of being carried out during treatment beam delivery. This system may also be referred to as an RT Ultimate (RTU) system for convenience. In an RTU system, a third gantry, which may be referred to as an RT gantry, is added in between CT source gantry 208 and CT detector gantry 209.

Figure 3:
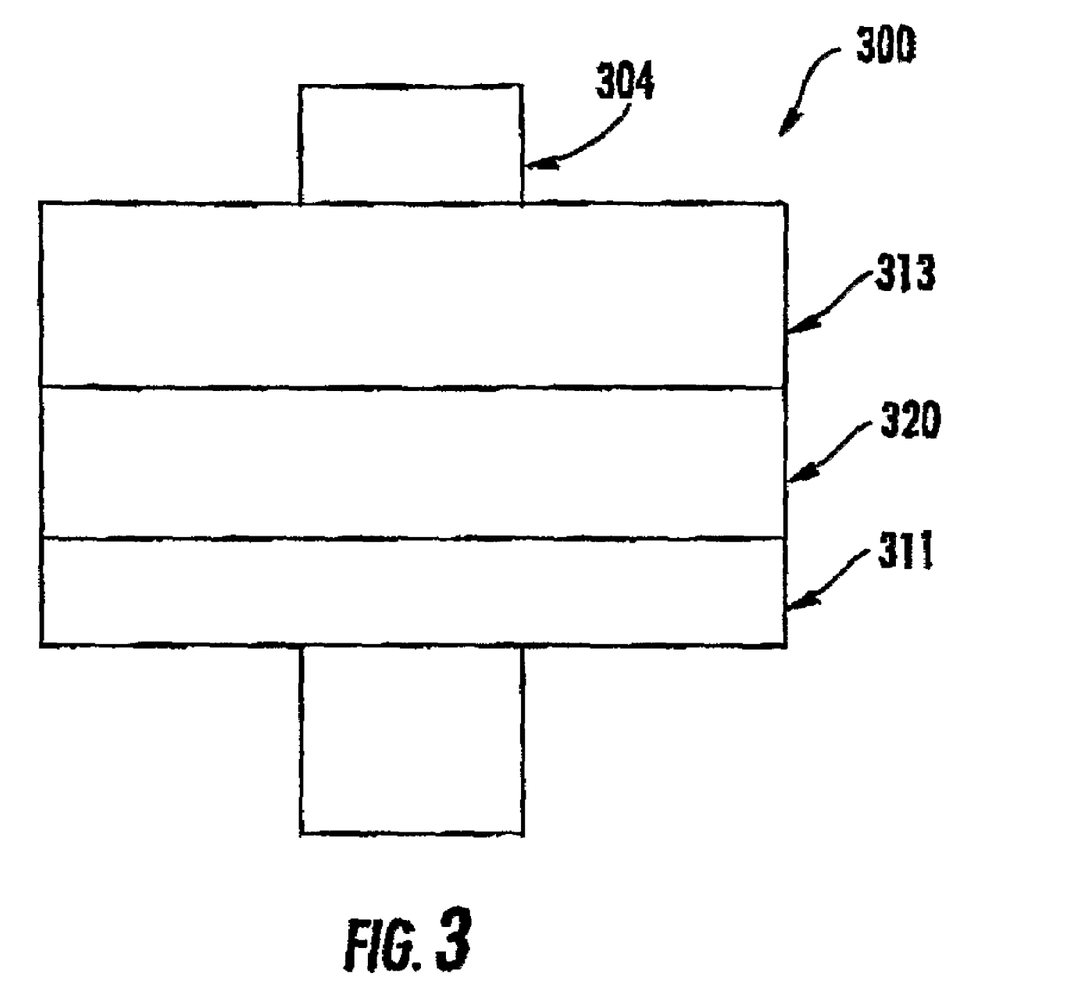
FIG. 3 shows a top view of a beveled computerized tomography system according to another embodiment of the present invention.
Figure 4:
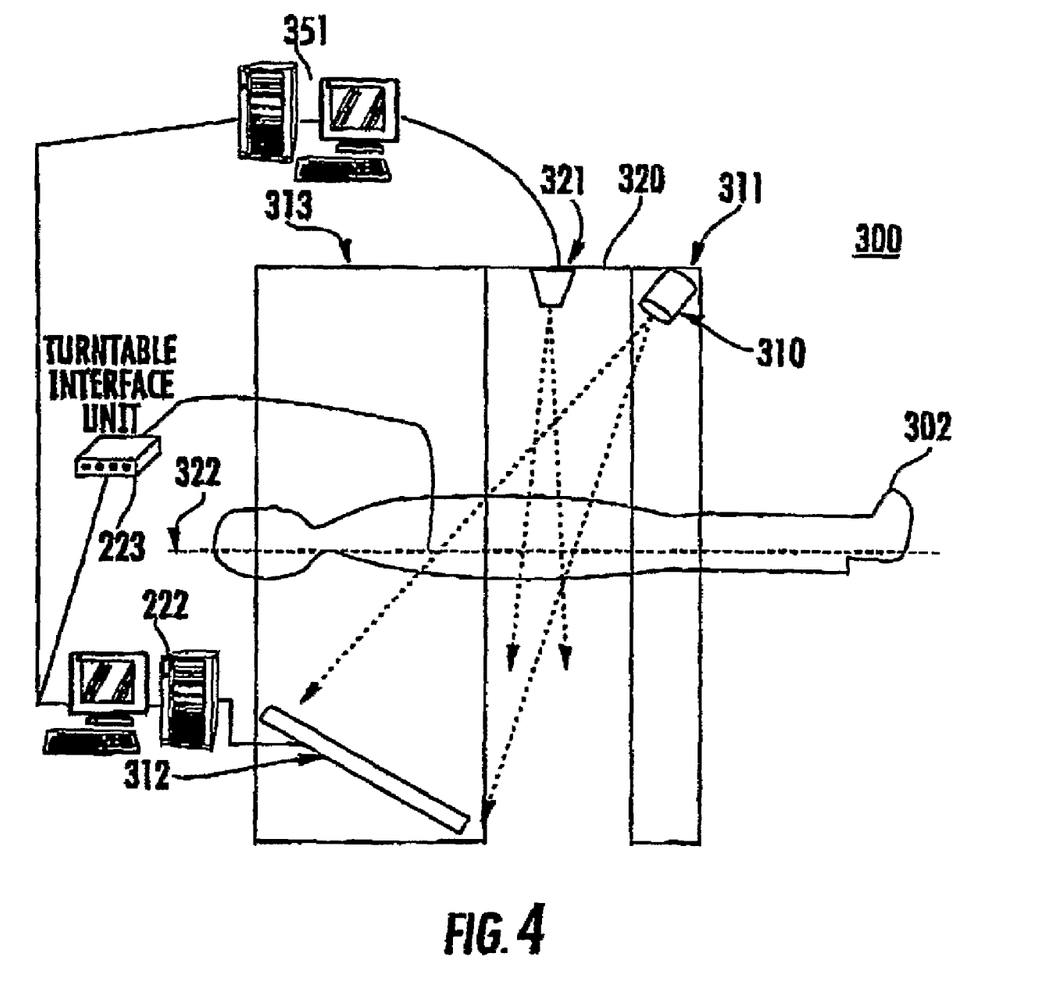
FIG. 4 shows a side view of a radiation therapy system according to the embodiment set forth in FIG. 3.

FIGS. 3 and 4 show a top view and a side view, respectively, of an RTU system 300 according to one embodiment of the present invention. As may be seen in FIG. 3, the system 300 includes a CT source gantry 311 for housing the x-ray or other CT source 310, a CT detector gantry 313 for housing the x-ray detector or other CT detector 312, and an RT source gantry 320 for housing the radiation therapy source 321. The radiation therapy source 321 may be any radiation therapy source including, but not limited to, a linear accelerator, a cobalt therapy unit, or any other radioactive isotope radiation source. As may be seen from FIG. 3, the patient (not shown) rests on a table 304 and the CT source gantry 311 and CT detector gantry 313 are separated by the RT source gantry 320.

As may be seen better from FIG. 4, as the CT source gantry 311 and CT detector gantry 313 are separated, emissions from the x-ray source 310 are angled with respect to the plane of the patient 302, and this angle is not a perpendicular angle. As a result, the CT detector panel 312 is also angled with respect to the plane 322 of the patient 302, and this angle is also not a perpendicular angle. As with system 200 shown in FIG. 2, system 300 communicates the analog video signal provided by detector 312 (detector 212 in FIG. 2) to PC 222, with the output of PC 222 being communicably connected to turntable interface unit 223 which controls the position of table 203 which holds the patient via computer controlled turntable.

PC 222 is connected to PC or other computing and control structure 351. PC 351 receives position data from PC 222 regarding patient and uses the position data improve control of radiation therapy source 321. For example, if patient 302 moves during a radiation therapy procedure, one or more parameters of the radiation therapy beam output by source 321 can be modified, such as the position of the beam to redirect the beam to the target location on patient 302.

System 300 permits the area of interest of the patient 302 to be accessed and treated by the radiation therapy source 321, which may be directed at an angle substantially perpendicular to the patient, which is the standard CT scanning angle in prior art systems. As a result, image guided radiation therapy may be performed wherein CT scanning (which provides position data) is occurring substantially simultaneously with RT treatment, thereby resulting in a more accurate radiation therapy treatment system.

Other embodiments of an RTU system may also be used based upon the advantages present in the beveled CT system of the present invention. For example, in one embodiment (not shown), the RT gantry may contain multiple radiation treatment sources. Any of the RT sources 321 previously mentioned, such as a linear accelerator or radioactive isotope source, may be utilized as the radiation source 321. Each source may be designed to rotate both concurrently and independently. If independent rotation is used, it will generally be limited to the adjacent source.

In an alternative embodiment wherein field shaping may be beneficial, a multi-leaf collimator (MLC) may be used for each source. In most current radiation therapy systems, one of the most time consuming steps is the rotation of the gantry. Accordingly, in this embodiment, by installing multiple sources, the amount of gantry rotation may be minimized, resulting in efficient beam delivery. This system may also decrease the chance of patient intra-fraction displacement, which is very beneficial in modern high-precision radiation therapy.

One of the disadvantages of current radiation therapy systems that are equipped with an MLC system is that the MLC system significantly increases machine down time because of its high failure rate. When MLC malfunctions, it is not possible to continue a high-precision therapy such as IMRT (intensity modulated radiation therapy). However, in the RTU system of the present invention, the treatment can continue using any functioning MLC. As there is an increased number of MLCs, the likelihood of all MLCs malfunctioning at the same time is significantly reduced.

In an alternative embodiment of the invention an electrical portal imaging device (EPID) may be installed for each RT source. An EPID may be used to improve the alignment of the radiation beam with respect to a tumor during radiation treatment. EPIDs are commercially available. In this inventive embodiment, the EPIDs provide images of the patient using the RT beam. EPIDs provides planar image quality which is generally not very high, but can provide a quick check for bony anatomy. A CT is also preferably provided since the CT provides accurate volumetric image which permits a more accurate setup and real time adjustments during the actual procedure to be achieved. Each EPID may be rotated independently, such as using an independent mechanical system inside the gantry. Therefore, the EPIDs can be positioned either in or out of the treatment field as needed.

Figure 5:
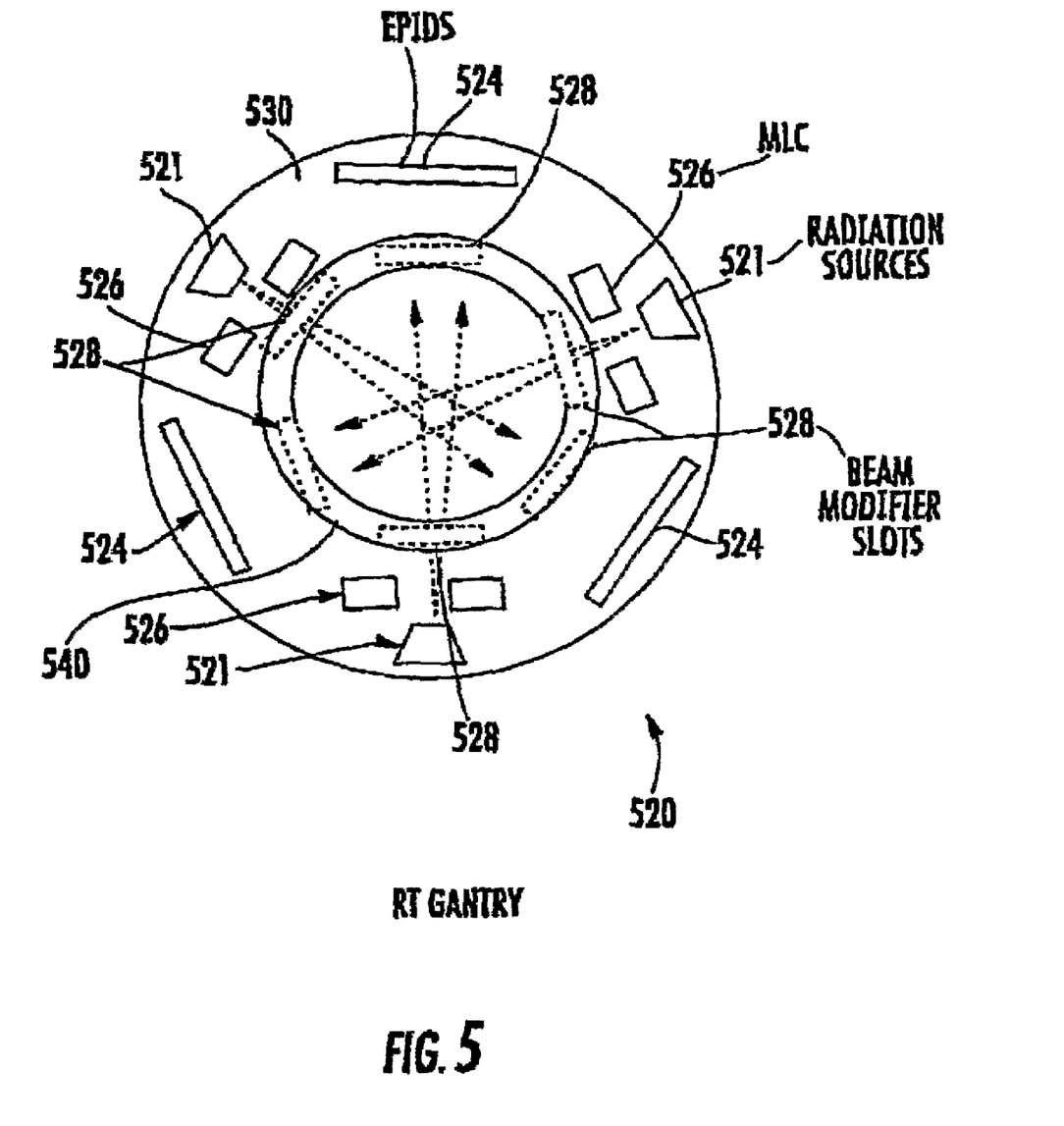
FIG. 5 shows a transversal view of a radiation therapy gantry according to one aspect of the present invention.

FIG. 5 shows a transverse view of a RT gantry 520 having multiple radiation sources according to one embodiment of the present invention. The RT gantry 520 comprises two rings, outer ring 530 and inner ring 540. Inner ring 540 is connected to outer ring 530 to permit independent rotation, such as using rotating bearings (not shown). RT gantry 520 call be integrated into system 300 by replacing RT gantry 320 with RT gantry 520. RT gantry 520 is shown including three (3) radiation therapy sources 521, three (3) EPIDs 524, three (3) MLCs 526, and six (6) beam modifier slots 528. However, it is to be understood that the number of radiation therapy sources, EPIDs, MLCs, and/or beam modifier slots (also referred to as "compensator blocks") may vary as needed depending on the selected parameters of the final system. In addition, while the number of beam modifier slots may be greater than that of the number of radiation sources, this is not required and alternative embodiments may include RT systems having the same number or fewer beam modifier slots than that of the number of radiation sources.

As noted above, slots 528 are designed to rotate independently from the radiation sources 521. When IMRT is delivered using modifier slots 528, all modifier slots may be mounted at the same time. For each beam angle, different modifier slots 528 are needed. If multiple fields are used, multiple modifier slots are needed. Because there are multiple slots 528 in gantry 520, tip to six (6) modifier slots can be preloaded.

In alternative embodiments, the beveled CT system and method may be used in conjunction with nuclear imaging modalities. Examples of nuclear imaging modalities that may be used in the present invention include, but are not limited to, emission tomography technologies, such as Single Photon-Emission Tomography (SPECT) and Positron Emission Tomography (PET).

PET measures the emission of positrons from the patient after a small amount of radioactive isotopes, or tracers, have been injected into the blood stream. This technique has proven extremely useful in research regarding functioning of organs. However, the half-lives of the isotopes used are very short. SPECT is closely related to PET, but uses isotopes with longer half-lives that can be stored on site. However, its resolution is generally lower, yielding less detailed images. As such, it would be beneficial to perform CT scanning during either SPECT or PET to provide real time patient contour and attenuation information during SPECT or PET. The present invention is capable of performing these techniques, which is an improvement over earlier systems wherein SPECT/CT and PET/CT scans must be carried out in series.

In yet another embodiment, the beveled CT system and method may be used in an operating room without anything located between the two gantries. As such, a real time CT scan may be performed with minimum interruption of operation procedure. As a result, real time CT image guided surgery may be performed. This embodiment may be used with any surgical procedure in which CT imaging may be beneficial during surgery.

It is to be understood that while the invention has been described in conjunction with the specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

I claim:

1. A computed tomography (CT) system, comprising:
   a table for holding a patient, said table oriented along a plane, said plane including a longitudinal axis;
   a first gantry housing a radiation source which emits penetrating radiation;
   a second gantry, spaced apart from said first gantry, housing a penetrating radiation detector for receiving said penetrating radiation after passing through said patient, wherein said first and second gantry are separate and disposed along said longitudinal axis;
   wherein said penetrating radiation from said radiation source is angled through said table at a non-perpendicular angle with respect to a said longitudinal axis of said table.

2. The system of claim 1, further comprising a third gantry spaced apart from said first and said second gantry including at least one radiation therapy source or other imaging system, wherein said third gantry is located between said first gantry and said second gantry.

3. The system of claim 2, wherein said radiation therapy source is a linear accelerator or a radioactive isotope source.

4. The system of claim 2, wherein said other imaging system comprises an emission tomography system.

5. The system of claim 4, wherein said emission tomography system comprises a Single Photon-Emission Tomography system or a Positron Emission Tomography system.

6. The system of claim 2, wherein said third gantry comprises a plurality of said radiation therapy sources.

7. The system of claim 6, wherein each of said plurality of radiation therapy sources is provided a multileaf collimator.

8. The system of claim 6, wherein said third gantry comprises an outer ring and an inner ring, wherein said inner and outer rings are independently rotatable.

9. The system of claim 8, wherein said outer ring includes said plurality of radiation sources and said inner ring comprises a plurality of beam modifier slots.

10. The system of claim 8, wherein said outer ring includes a plurality of electrical portal imaging devices (EPIDs).

11. A method of performing substantially real-time CT image guided treatment on a patient, comprising the steps of:
    providing a computed tomography system comprising a first gantry housing a radiation source which emits penetrating radiation and a second gantry, spaced apart from said first gantry, housing a penetrating radiation detector for receiving said penetrating radiation after passing through said patient, wherein said first and second gantry are separate and disposed along said longitudinal axis, wherein said penetrating radiation from said system is angled through a patient on said table at a non-perpendicular angle with respect to a longitudinal axis of a table holding said patient, and
    performing a treatment or other imaging step on said patient while performing CT imaging using guidance from images generated by said CT system.

12. The method of claim 11, wherein said treatment step or other imaging step comprises radiation therapy, emissions tomography, a surgical procedure, or a combination thereof.

13. The method of claim 11, wherein said treatment step is a radiation therapy delivered by a linear accelerator treatment or a radioactive isotope source.

14. The method of claim 11, wherein said other imaging step comprises emission tomography treatment selected from Single Photon-Emission Tomography or Positron Emission Tomography.

15. The method of claim 11, wherein said treatment or other imaging step comprises using a third gantry separate from said first gantry and second gantry, wherein said third gantry (i) includes at least one radiation therapy source or other imaging system, and (ii) is located on said longitudinal axis between said first gantry and said second gantry.

16. A computed tomography (CT) system, comprising:
- a table for holding a patient, said table oriented along a plane, said plane including a longitudinal axis;
- a first gantry housing a radiation source which emits penetrating radiation;
- a second gantry, spaced apart from said first gantry housing a penetrating radiation detector for receiving said penetrating radiation after passing through said patient; and
- a third gantry spaced apart from said first and said second gantry including at least one radiation therapy source or other imaging system, wherein said first and second gantry are disposed at non-overlapping positions along said longitudinal axis, wherein said third gantry is located between said first gantry and said second gantry, and wherein said penetrating radiation from said radiation source is angled at a non-perpendicular angle with respect to a said longitudinal axis of said table.

* * * * *